US010856799B2

(12) United States Patent
Tey et al.

(10) Patent No.: US 10,856,799 B2
(45) Date of Patent: Dec. 8, 2020

(54) THREE-DIMENSIONAL REPRESENTATION OF SKIN STRUCTURE

(71) Applicants: AGENCY FOR SCIENCE, TECHNOLOGY AND RESEARCH, Singapore (SG); NATIONAL SKIN CENTRE (SINGAPORE) PTE LTD, Singapore (SG)

(72) Inventors: Hong Liang Tey, Singapore (SG); Ruchir Srivastava, Singapore (SG); Ai Ping Yow, Singapore (SG); Jun Cheng, Singapore (SG); Annan Li, Singapore (SG); Wing Kee Damon Wong, Singapore (SG); Jiang Liu, Singapore (SG); Carolin Wall, Singapore (SG)

(73) Assignees: Agency for Science, Technology and Research, Singapore (SG); National Skin Centre (Singapore) PTE LTD, Singapore (SG)

( * ) Notice: Subject to any disclaimer, the term of this patent is extended or adjusted under 35 U.S.C. 154(b) by 113 days.

(21) Appl. No.: 16/090,172

(22) PCT Filed: Mar. 28, 2017

(86) PCT No.: PCT/SG2017/050166
§ 371 (c)(1),
(2) Date: Sep. 28, 2018

(87) PCT Pub. No.: WO2017/171643
PCT Pub. Date: Oct. 5, 2017

(65) Prior Publication Data
US 2019/0110739 A1    Apr. 18, 2019

(30) Foreign Application Priority Data

Mar. 28, 2016    (SG) .......................... 10201602395 U (51) Int. Cl.
*A61B 5/00*    (2006.01)
*G06T 7/00*    (2017.01)
(Continued)

(52) U.S. Cl.
CPC ............ *A61B 5/442* (2013.01); *A61B 5/0066* (2013.01); *G06T 7/0012* (2013.01); *G06T 7/12* (2017.01);
(Continued)

(58) Field of Classification Search
CPC ... A61B 5/442; A61B 5/0066; A61B 2576/02; G06T 7/0012; G06T 7/12; G06T 7/162; G06T 2207/10101; G06T 2207/30088
See application file for complete search history.

(56) References Cited

U.S. PATENT DOCUMENTS

2005/0243327 A1* 11/2005 Li ........................ A61B 5/0059
356/496
2007/0058865 A1    3/2007 Li et al.
(Continued)

FOREIGN PATENT DOCUMENTS

CN        103854284 A       6/2014
WO    WO 2015/001317 A1    1/2015

OTHER PUBLICATIONS

PCT International Search Report for PCT Counterpart Application No. PCT/SG2017/050166, 3 pgs. (dated Jun. 20, 2017).
(Continued)

*Primary Examiner* — Wesley J Tucker
(74) *Attorney, Agent, or Firm* — Womble Bond Dickinson (US) LLP (57) ABSTRACT

The present disclosure generally relates to an automated method and system for generating a three-dimensional (3D) representation of a skin structure of a subject. The method comprises: acquiring a plurality of two-dimensional (2D) cross-sectional images of the skin structure, specifically, using optical coherence tomography (OCT) technique; computing a cost for each 2D cross-sectional image based on a cost function, the cost function comprising an edge-based parameter and a non-edge-based parameter; constructing a 3D graph from the 2D cross-sectional images; and determining a minimum-cost closed set from the 3D graph based
(Continued)

on the computed costs for the 2D cross-sectional images, wherein the 3D representation of the skin structure is generated from the minimum-cost closed set.

20 Claims, 9 Drawing Sheets (51) Int. Cl.
 G06T 7/12 (2017.01)
 G06T 7/162 (2017.01)
(52) U.S. Cl.
 CPC .......... *G06T 7/162* (2017.01); *A61B 2576/02* (2013.01); *G06T 2207/10101* (2013.01); *G06T 2207/30088* (2013.01)

(56) References Cited

U.S. PATENT DOCUMENTS

2009/0021724 A1\* 1/2009 Mahadevan-Jansen ..................... A61B 5/0066 356/73

2019/0336063 A1\* 11/2019 Dascalu ............... A61B 5/7267

OTHER PUBLICATIONS

PCT Written Opinion for PCT Counterpart Application No. PCT/SG2017/050166, 5 pgs. (dated Jun. 20, 2017).
A.P. Yow, et al., "Skin Surface Topographic Assessment using in vivo High-Definition Optical Coherence Tomography," 2015 10th International Conference on Information, Communications and Signal Processing (ICICS), 4 pgs. (Dec. 4, 2015).
M.K. Garvin, et al., "Intraretinal Layer Segmentation of Macular Optical Coherence Tomography Images Using Optimal 3-D Graph Search," IEEE Trans Med Imaging, vol. 27, No. 10, pp. 1495-1505 (Oct. 2008).
"Optimal Surface Segmentation in Volumetric Images—A graph-Theoretic Approach," IEEE Transactions on Pattern Analysis and Machine Intelligence, vol. 28, No. 1, pp. 119-134 (Jan. 2006).
A. Li, et al., "Epidermal Segmentation in High-Definition Optical Coherence Tomography," $37^{th}$ Annual International Conference on the IEEE Engineering in Medicine and Biology Society, p. 3045-3048 (Aug. 29, 2015).

\* cited by examiner

Figure 10

THREE-DIMENSIONAL REPRESENTATION OF SKIN STRUCTURE

CROSS REFERENCE TO RELATED APPLICATIONS

This patent application is a U.S. National Phase Application under 35 U.S.C. § 371 of International Application No. PCT/SG2017/050166, filed on 28 Mar. 2017, entitled THREE-DIMENSIONAL REPRESENTATION OF SKIN STRUCTURE, which claims the benefit of Singapore Patent Application No. 10201602395U filed on 28 Mar. 2016, which was incorporated in its entirety by reference herein.

TECHNICAL FIELD

The present disclosure generally relates to three-dimensional (3D) representation of skin structure. More particularly, the present disclosure describes various embodiments of an automated method and system for generating a 3D representation of the skin structure of a subject (e.g. human patient or candidate).

BACKGROUND

References

[1] Lévêque, J. L. (1999), *EEMCO guidance for the assessment of skin topography*. Journal of the European Academy of Dermatology and Venereology, 12: 103-114. doi: 10.1111/j.1468-3083.1999.tb00998.x

[2] Takanori Igarashi, Ko Nishino, Shree K. Nayar, *The Appearance of Human Skin: A Survey, Foundations and Trends® in Computer Graphics and Vision*, v. 3 n. 1, p. 1-95, January 2007

[3] J. Weissman, T. Hancewicz, and P. Kaplan. Optical coherence tomography of skin for measurement of epidermal thickness by shapelet-based image analysis. Optics express, 12(23):5760-5769, 2004.

[4] Y. Hori, Y. Yasuno, S. Sakai, M. Matsumoto, T. Sugawara, V. Madjarova, M. Yamanari, S. Makita, T. Yasui, T. Araki, et al. Automatic characterization and segmentation of human skin using three-dimensional optical coherence tomography. optics express, 14(5):1862-1877, 2006.

[5] A. Mcheik, C. Tauber, H. Batatia, J. George, and J.-M. Lagarde. Speckle modelization in OCT images for skin layers segmentation. In VISAPP (1), pages 347-350, 2008.

[6] A. Li, J. Cheng, A. P. Yow, C. Wall, D. Wong, H. Tey, and J. Liu. Epidermal segmentation in high-definition optical coherence tomography. In IEEE EMBC, 2015.

[7] A. P. Yow, J. Cheng, A. Li, C. Wall, D. Wong J. Liu and H. Tey, Skin Surface Topographic Assessment using in vivo High-Definition Optical Coherence Tomography. In 17th International Conference on Information and Computer Security, 2015.

[8] Lioudmila Tchvialeva, Haishan Zeng, Igor Markhvida, David I McLean, Harvey Lui and Tim K Lee (2010). *Skin Roughness Assessment*, New Developments in Biomedical Engineering, Domenico Campolo (Ed.), ISBN: 978-953-7619-57-2, InTech

[9] Boone, Marc A L M, et al. *High-definition optical coherence tomography* 15 *imaging of melanocytic lesions: a pilot study*. Archives of dermatological research (2013): 1-16.

[10] Y. Boykov and V. Kolmogorov. An experimental comparison of min-cut/max-flow algorithms for energy minimization in vision. Pattern Analysis and Machine Intelligence, IEEE Transactions on, 26(9):1124-1137, 2004.

The skin is the outer covering of a human body and is the largest organ of the integumentary system. Skin characteristics can vary due to numerous factors [References 1, 2] such as malignancy, ageing, cosmetics, and personal care products. Hence, the evaluation of the human skin structure and surface topography is of particular importance to dermatological, cosmetic, pharmaceutical, and/or cosmeceutical practice and research.

Optical coherence tomography (OCT) has emerged as a useful non-invasive imaging modality for medical image analysis, including for human skin structure and surface. OCT provides a higher resolution than ultrasound and deeper penetration than confocal microscopy images, and provides an ideal balance between penetration depth and resolution. OCT images are manually examined by dermatologists/clinicians for detecting abnormalities in the skin or assessing response of skin to treatments or and/or cosmetics products. However, manual examination is burdensome and subjective. Computerized analysis of OCT images can be used as a screening tool to assist dermatologists/clinicians. Such screening can filter out the obvious healthy cases and refer the more serious or less than-healthy cases to the dermatologists/clinicians.

Figure 1A:
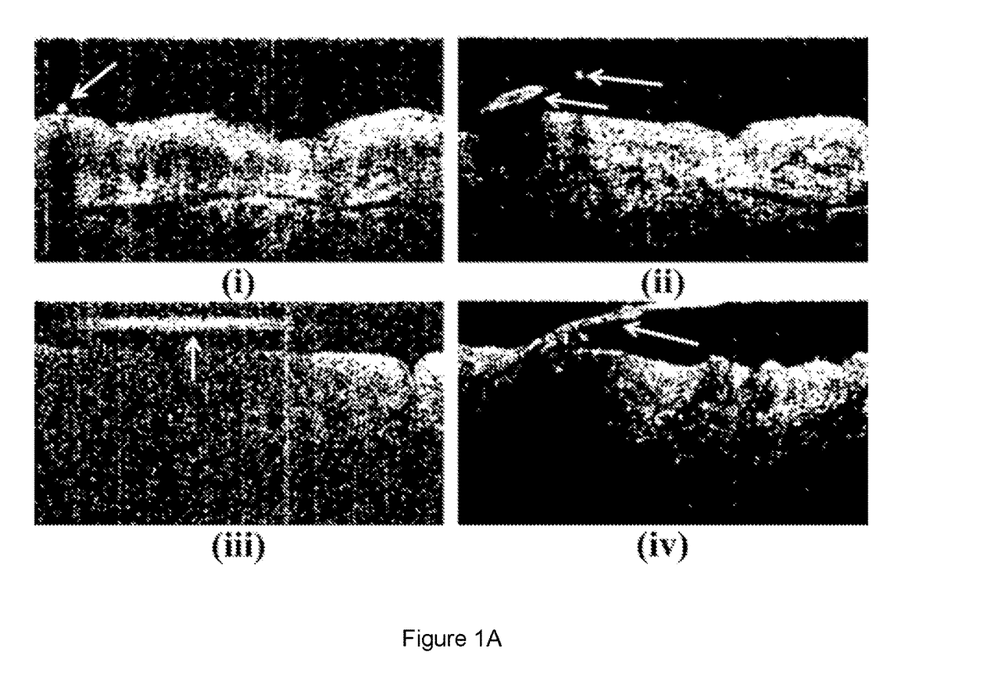
FIG. 1A illustrates different appearances of hair in various OCT images of a skin structure.

One of the major challenges in analyzing OCT images of the skin is the presence of body hair. This is especially relevant when assessing hairy areas of the body (such as the face, outer aspects of the forearms and calves, chest, and the back of the hands) or in imaging scalp diseases. Hair obstructs imaging of the skin resulting in poor contrast in some parts of the skin structure as shown in FIG. 1A (hairs are indicated by arrows).

For computerized screening in dermatological applications, the skin structure is segmented to identify the different layers of the skin structure, because there are certain skin conditions which are observed in specific layers. The major layers of the skin structure are stratum-corneum, epidermis, and dermis. Epidermal thickness measurement is important for assessing skin health, ageing and photodamage. Measurement of the epidermal thickness is possible by segmenting the dermoepidermal junction (DEJ) which is the boundary between epidermis and dermis. DEJ segmentation depends on accurate segmentation of skin structure since the external skin surface provides a constraint for epidermis segmentation.

Skin structure segmentation is thus performed as a part of measuring the epidermal thickness. Conventional techniques use shapelets [Reference 3] to segment the skin structure or use intensity values [Reference 4] for the segmentation. While some techniques [Reference 5] attempt to characterize layers of the skin structure using speckle noise distribution but do not really segment the skin structure.

Figure 1B:
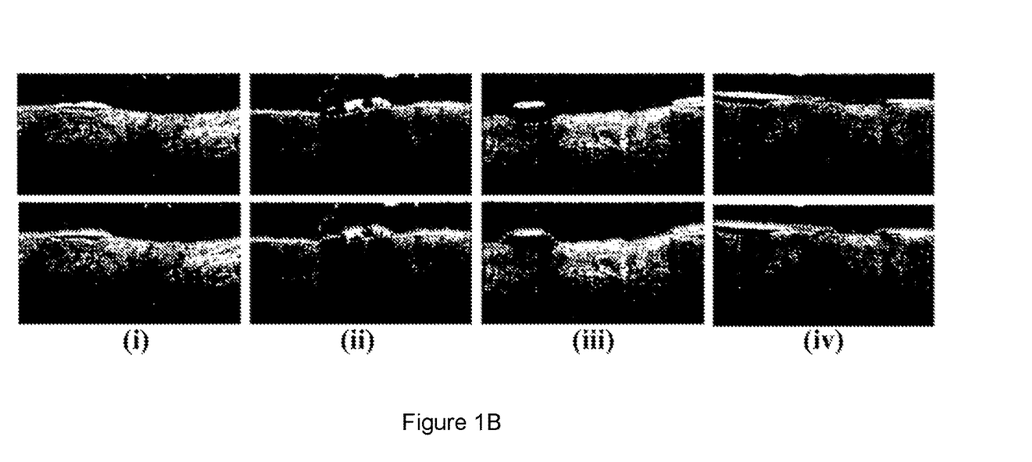
FIG. 1B illustrates various images of skin segmentation failures due to presence of hair.

Other existing methods [Reference 6] employ a graph-based method for skin surface segmentation whereby vertical intensity gradients are used in the cost function. In another existing graph-based method [Reference 7], vertical intensity gradients and gradient magnitude are used in the cost function. These methods have not considered the presence of body hair which can cause significant errors in profiling the skin structure and surface as shown in FIG. 1B. Current clinical practice is to remove hair by shaving. However, shaving causes skin flakes which can induce inaccuracies in skin surface topography analysis.

Irregularities in skin surface topography constitute roughness and wrinkles observable by the human eye. Skin surface roughness and wrinkles is an important evaluation item in evidence reports on the progress of dermatological treatment. In most clinical settings, skin surface roughness and wrinkles are primarily assessed by visual inspection, with a critical dependence on dermatologists'/clinicians' experiences. Besides visual inspection, roughness and wrinkles can also be quantitatively measured indirectly from skin replicas [Reference 8] which are produced by imprinting the skin surface onto a silicone material. Roughness measurement is then performed on the skin replicas using a mechanical profilometry approach or optical techniques such as microphotography. However, replica-based methods are inconvenient in clinical settings and susceptible to distortions (including the presence of air bubbles) during skin replica reproduction, and require long scanning times [Reference 1].

Direct in vivo methods may be employed for analyzing the skin surface topography. One existing method used for in vivo skin analysis is fringe projection area topography [Reference 3]. Examples of such area topography systems include PRIMOS® and DermaTOP®. Despite having a fast acquisition time of less than 1 second, the drawbacks of such fringe projection methods are the interference of back scattering from skin tissue volume effects, the deformation of fringe image caused by micro body movement, and the low accuracy due to a moderate resolution of 15 to 24 μm [Reference 3].

More recently, high-definition OCT (HD-OCT) is available with an enhanced resolution of 3 μm in both axial and en face planes, allowing for better visualization of the skin structure [Reference 9] and a relatively fast image acquisition time of 2 to 3 seconds. With its high resolution and fast acquisition, HD-OCT can be used as a potential tool for precise analysis of the skin surface topography, particularly to assess irregularities in the skin surface topography.

Figure 2A:
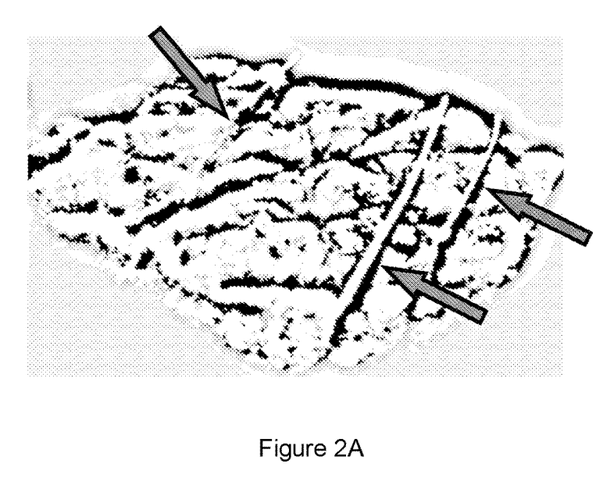
FIG. 2A illustrates a skin surface affected by presence of hair.
Figure 2B:
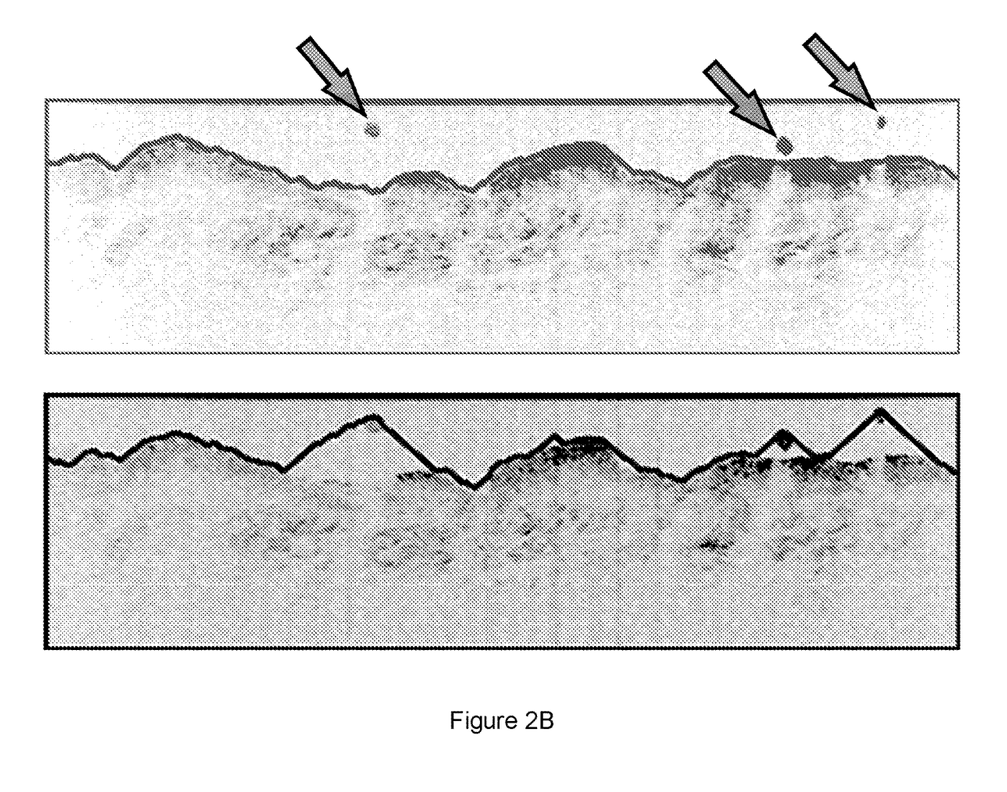
FIG. 2B illustrates a skin structure with a false skin surface boundary due to presence of hair.

As described above, one of the main challenges in analyzing skin surface topography is the presence of body hair on the skin surface. The presence of hair imaged during image acquisition may appear as bright blobs floating above the skin surface on the OCT images. This results in a shadow cast upon the skin surface, weakening the contrast of the edge at the skin surface, as shown in FIG. 2A (indicated by arrows). The strong edges of the hairs may also attract the path edges of the skin surface and lead to false detection of the skin surface boundary as shown in FIG. 2B. The upper image in FIG. 2B illustrates the presence of hair as blobs (indicated by arrows), and the lower image in FIG. 2B illustrates the false skin surface boundary due to the presence of hair.

Therefore, in order to address or alleviate at least one of the aforementioned problems and/or disadvantages, there is a need to provide an automated method and system for generating a 3D representation of a skin structure of a subject, in which there is at least one improvement and/or advantage over the aforementioned prior art.

SUMMARY

According to an aspect of the present disclosure, there is an automated method and system for generating a three-dimensional (3D) representation of a skin structure of a subject. The system comprises a processor configured for performing steps of the method. Steps of the method comprise: acquiring a plurality of two-dimensional (2D) cross-sectional images of the skin structure; computing a cost for each 2D cross-sectional image based on a cost function, the cost function comprising an edge-based parameter and a non-edge-based parameter; constructing a 3D graph from the 2D cross-sectional images; and determining a minimum-cost closed set from the 3D graph based on the computed costs for the 2D cross-sectional images, wherein the 3D representation of the skin structure is generated from the minimum-cost closed set.

An advantage of the present disclosure is that the 3D representation of the skin structure enables for more accurate analysis of the skin structure and surface, addressing one or more of the aforementioned limitations of existing methods in segmenting skin surface with hair. The 3D representation is formed by constructing a 3D graph from multiple 2D cross-sectional images such that information from neighbouring/adjacent images is considered. Since a single instance of hair is usually present in only a few consecutive images, collective consideration of all the images attenuate the effects of hair presence in some of the images, resulting in a more accurate representation of the skin structure and surface. Such information is neglected in existing surface methods because they are essentially 2D methods which are not robust to the presence of hair. The present disclosure thus provides for generation of a 3D representation of the skin structure wherein there is better accuracy in the segmentation of the skin structure, even in the presence of hair where existing 2D methods fail. The 3D representation generated from the 3D graph thus presents an improvement over existing 2D graph-based methods.

An automated method and system for generating a 3D representation of a skin structure of a subject according to the present disclosure are thus disclosed herein. Various features, aspects, and advantages of the present disclosure will become more apparent from the following detailed description of the embodiments of the present disclosure, by way of non-limiting examples only, along with the accompanying drawings.

DETAILED DESCRIPTION

In the present disclosure, depiction of a given element or consideration or use of a particular element number in a particular figure or a reference thereto in corresponding descriptive material can encompass the same, an equivalent, or an analogous element or element number identified in another figure or descriptive material associated therewith. The use of "/" in a figure or associated text is understood to mean "and/or" unless otherwise indicated. As used herein, the term "set" corresponds to or is defined as a non-empty finite organization of elements that mathematically exhibits a cardinality of at least one (e.g. a set as defined herein can correspond to a unit, singlet, or single element set, or a multiple element set), in accordance with known mathematical definitions. The recitation of a particular numerical value or value range herein is understood to include or be a recitation of an approximate numerical value or value range.

For purposes of brevity and clarity, descriptions of embodiments of the present disclosure are directed to an automated method and system for generating a three-dimensional (3D) representation of a skin structure of a subject, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

Figure 3:
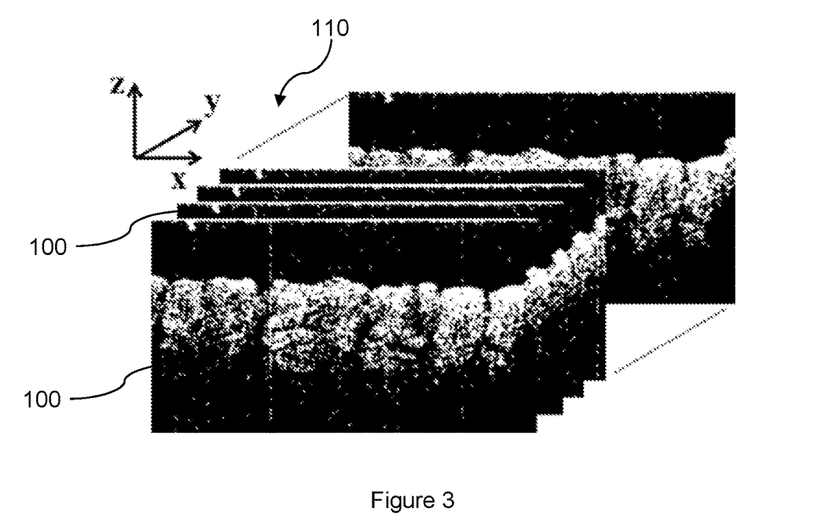
FIG. 3 illustrates an OCT volume having a plurality of 2D cross-sectional images of a skin structure.

In representative or exemplary embodiments of the present disclosure, there is a system including a processor, e.g. image processing module/component, for performing an automated method for generating a 3D representation of a skin structure of a subject. Referring to FIG. 3, a plurality of two-dimensional (2D) cross-sectional images 100 of the skin structure is acquired or captured using an optical coherence tomography (OCT) technique. The 2D cross-sectional images 100 are captured as a series of B-scans and may also be referred to as cross-sectional tomographs or slices. The 2D cross-sectional images 100 collectively form an OCT volume 110. As shown in FIG. 3, each 2D cross-sectional image or slice 100 is along the x-z plane and the 2D cross-sectional images in the OCT volume 110 stack along the y-direction.

Figure 4:
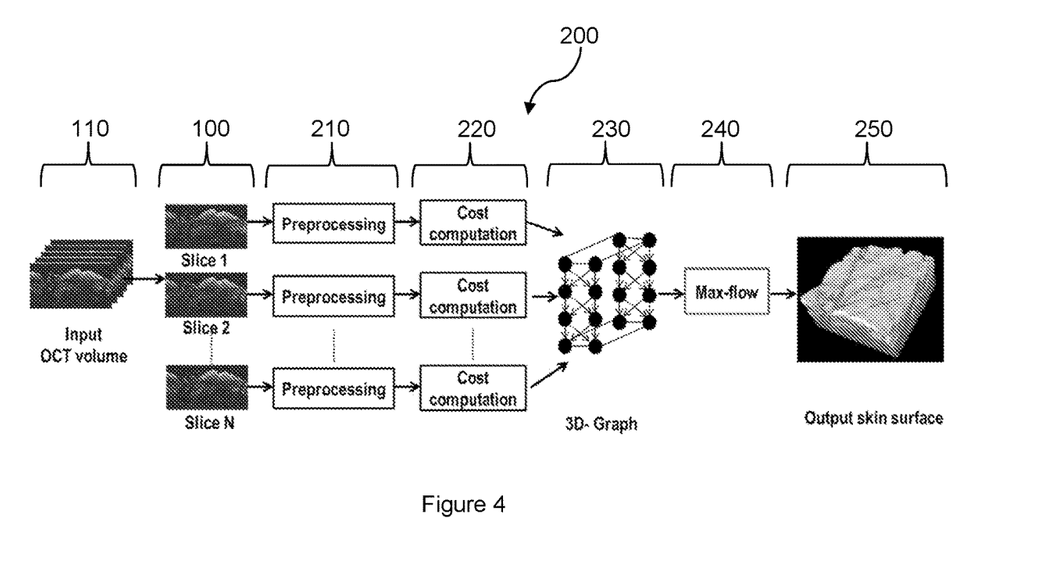
FIG. 4 illustrates a flowchart of a method for generating a 3D representation of a skin structure of a subject.

FIG. 4 illustrates a flowchart of an automated method 200 performed by the processor for generating a 3D representation of the skin structure. After the 2D cross-sectional images 100 in the OCT volume 110 are acquired, each 2D cross-sectional image 100 is subject to a preprocessing stage or phase 210 of the method 200. The 2D cross-sectional images 100 may be captured using the OCT technique in 16-bit resolution, e.g. in 16-bit grayscale. In the preprocessing stage 210, each 2D cross-sectional image 100 is converted to 8-bit grayscale. The contrast of each 2D cross-sectional image 100 is then enhanced using contrast stretching or normalization.

In one embodiment, in the preprocessing stage 210, 2D graphs may be constructed from the plurality of 2D cross-sectional images 100 of the skin structure. A 2D graph represents or corresponds to a 2D cross-sectional image 100. Each 2D graph includes a plurality of nodes, each node corresponding to a pixel of the corresponding 2D cross-sectional image 100. The nodes are connected through edges.

The method 200 further includes a cost computation stage or phase 220 after the preprocessing stage 210. In the cost computation stage 220, a cost for each 2D cross-sectional image 100 is computed based on a cost function, the cost function including an edge-based parameter and a non-edge-based parameter. Details of the cost function are elaborated below.

After the cost computation stage 220, a 3D graph 230 is constructed from the 2D cross-sectional images 100. In another embodiment, the 3D graph 230 may be constructed from the 2D graphs which are in turn constructed from the 2D cross-sectional images. The 3D graph 230 represents or corresponds to the OCT volume 110. As with 2D graphs, the 3D graph 230 includes a plurality of nodes, each node corresponding to a voxel of the OCT volume 110. The nodes are connected through edges.

The method 200 further includes a subsequent step 240 of determining a minimum-cost closed set from the 3D graph 230 based on the computed costs for the 2D cross-sectional images 100. The minimum-cost closed set is determined using the standard max-flow min-cut theorem or algorithm [Reference 10] which would be readily understood by the skilled person. An output skin structure and surface 250 is generated from the minimum-cost closed set. This output skin structure 250 is also the 3D representation 250 of the skin structure. The 3D representation 250 includes a plurality of voxels, each voxel corresponding to one of the nodes of the 3D graph 230. Furthermore, the 3D representation 250 corresponds to the desired skin structure of the subject which can be subsequently analyzed to assess skin health and/or various skin conditions of the subject.

In embodiments of the present disclosure, the following notations and terms are used to describe various aspects of the method 200.

$N_x$, $N_z$: Size of 2D cross-sectional image 100 along x and z directions, respectively.

I(x, y, z): 3D representation 250 of the skin structure representing the OCT volume 110 with I(x, y, z) being the intensity at a voxel (x, y, z). Here $x \in \mathbb{x} = \{1, 2, \ldots N_x\}$ represents the voxel indices along the x-axis. y and z are similarly defined.

$\mathcal{N}$: (x,y)→$\mathcal{N}$ (x,y): Function defining a surface where $\mathcal{N}$ (x,y)∈$\mathbb{z}$.

G=(V, E): 3D graph 230 representing I.

V(x, y, z): Node in G corresponding to voxel (x, y, z).

Column: Set of nodes with same (x, y) values. In the context of a 2D cross-sectional image 100, a column refers to all pixels with the same value of x.

Base layer: Set of all nodes corresponding to z=0.

C: A closed set C is the set of all those nodes such that the successors of each node in C are also contained in C.

$\Delta_x$, $\Delta_y$: Constants determining smoothness of the skin surface along x (within a 2D cross-sectional image 100) and y (across adjacent 2D cross-sectional images 100) directions, respectively.

c(x, y, z): Cost function for a voxel (x, y, z).

$c_y(x,z)$: Cost function for a 2D cross-sectional image 100 corresponding to y=Y.

w(x, y, z): Weight assigned to the node V(x, y, z).

In the 3D graph 230 or G=(V, E), V denotes the nodes while E denotes the edges. Each voxel in I has a corresponding node in the 3D graph 230. Each node V is connected only to its neighbouring nodes through the edges E. In a 4-neighbour setting, V(x, y, z) is connected to 4 neighbours outside its own column, namely (i) V(x−1, y, z−$\Delta_x$), (ii) V(x+1, y, z−$\Delta_x$), (iii) V(x, y−1, z−$\Delta_y$), and (iv) V(x, y+1, z−$\Delta_y$). In addition, each node (except for nodes in the base layer) is also connected to the node just below it, i.e. V(x, y, z) is connected to V(x, y, z−1). These edges enforce the smoothness constraints. This means that for a voxel (x, y, z) on a surface $\mathcal{N}$, its neighbouring voxels along the x-direction, i.e. (x+1, y, z') and (x−1, y, z''), are not lower than the voxel (x, y, max(0, z−$\Delta_x$)).

A cost can be computed for each node in the cost computation stage 220. The choice of the cost function used in the cost computation stage 220 is crucial for accurate generation of the 3D representation 250 of the skin structure. In order to find the minimum closed set, cost function has to be chosen such that it has a low value for voxels on the desired skin structure and a high value elsewhere. Usually, the appearance of the surface of the skin structure in a 2D cross-sectional image 100 is characterized by a surface profile with prominent edges. This characteristic can be captured by using the edge-based parameter in the cost function. However, for skin structures, there are other layers which can have strong gradients near their boundaries. To distinguish these layers from the skin surface, the cost function also includes a non-edge-based parameter.

Figure 5:
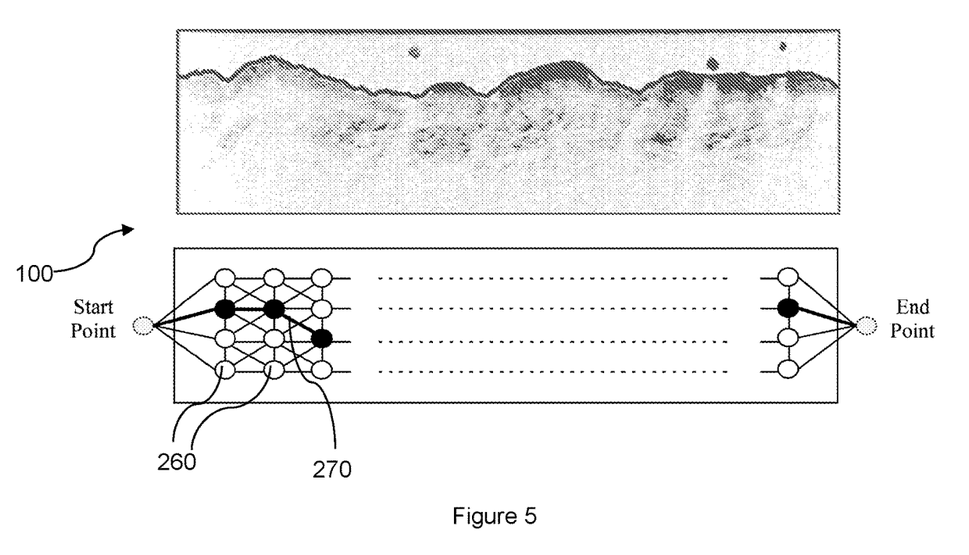
FIG. 5 illustrates a 2D cross-sectional image.

FIG. 5 illustrates a 2D cross-sectional image 100 with the surface of the skin structure characterized by the surface profile. FIG. 5 further illustrates a 2D cross-sectional image 100 having a plurality of nodes 260 and a plurality of edges 270. A weight value is assigned to each edge 270 to represent the cost to path through the edge. To travel between the nodes 260, the total cost is the sum of all weight values assigned to the edges 270 connecting the nodes 260. Due to the presence of hairs which may attract the pathing and lead to false detection of the skin surface profile or boundary, the edges 270 have to be assigned with appropriate weight values.

A high cost is assigned to non-edge nodes/pixels. A mask M(x, y) is computed as follows:

$$M(x, y) \begin{cases} 1 & 0 \leq grad(x, y) < T \\ 0 & \text{otherwise} \end{cases} \quad [1]$$

The weight v(x, y) for an edge 270 between two nodes 260 is calculated based on the gradients at the nodes 260 as follows:

$$v(x,y)=2-\text{grad}(x,y)-\text{grad}(x_n,y_n)+\lambda \cdot M(x,y)+\varepsilon \quad [2]$$

where grad(x, y) is the vertical gradient of the 2D cross-sectional image 100 at (x, y), grad($x_n$, $y_n$) is the vertical gradient of the 2D cross-sectional image 100 at node ($x_n$, $y_n$), $\lambda$ is a tuning parameter controlling the weight of the mask M(x, y), and $\varepsilon=10^{-5}$ is the minimum weight in the 2D cross-sectional image 100 added for stabilization. T may be set at 3 as the performance has been empirically shown to be insensitive to very small T ranging from 1 to 5. $\lambda$ may be set at 100, which is also empirically shown to be insensitive to the performance.

Equation [2] assigns low weight values to node pairs with large vertical gradients. In one example implementation, the gradients are normalized to values between 0 and 1. These weights are further adjusted to account for the directionality of the gradient. In some cases, if it is known that a boundary of the skin structure exhibits a dark to bright transition, only the dark to bright gradient is computed. After assigning the weight values, graph search algorithms such as the max-flow min-cut algorithm are used to determine the minimum path that connects the two endpoints.

The cost is thus computed for all nodes 260 of the 2D cross-sectional images 100. The 3D graph 230 is constructed from the 2D cross-sectional image 100. Notably, the cost for each node 260 corresponds to the cost for a pixel of the corresponding 2D cross-sectional image 100 and further corresponds to the cost for a voxel of the OCT volume 110.

The cost function $c_Y(x,z)$ for a 2D cross-sectional image 100 (along the x-z plane) can be defined as:

$$c_Y(x,z)=\rho \cdot c_Y^{edge}(x,z)+(1-\rho) \cdot c_Y^{non}(x,z) \quad [3]$$

where $c_Y^{edge}$ and $c_Y^{non}$ are the edge-based and non-edge-based parameters, respectively. The parameter $\rho$ controls the weightage given to the edge-based and non-edge-based parameters. The edge-based parameter is associated with the gradient information while non-edge-based parameter is associated with other information such as the homogeneity of the imaged portions above and below the skin surface.

The cost function thus has a combination of edge-based and non-edge-based parameters. When the edge-based parameter is included to the cost function for eventually generating the 3D representation 250 of the skin structure, the cost function gave a low cost to both the surface of the skin structure and another layer below it which also has an edge combined with a dark to bright transition. To avoid any confusion with the layers below the skin surface, the cost function includes the non-edge-based parameter to cooperate together with the edge-based parameter. This allows the skin surface to be clearly distinguished from the layers below it.

The edge-based and non-edge-based parameters are more specifically defined as follows:

$$c_Y^{edge}(x,z)=-e_Y(x,z) \cdot p(\phi_Y(x,z)) \quad [4]$$

$$c_Y^{non}(x,z)=b_Y(x,z)+r_Y(x,z) \quad [5]$$

The term p($\phi_Y$(x,z)) is an orientation penalty the term $\phi_Y$(x,z) is a gradient orientation. The orientation penalty p($\phi_Y$(x,z)) is a function of the gradient orientation $\phi_Y$(x,z) and is defined as:

$$p(\phi_Y(x,z)) = \begin{cases} 0, & \text{if } \phi_Y(x,z) = 270° \\ 1, & \text{if } 0° \leq \phi_Y(x,z) \leq 180° \\ <1 & \text{otherwise} \end{cases} \quad [6]$$

The orientation penalty p($\phi_Y$(x,z)) is defined in view of the dark to bright transition at the skin surface when traversing from top to bottom of the 2D cross-sectional image 100 (z is decreasing). At this dark to bright transition, the gradient orientation $\phi_Y$(x,z) is expected to vary from 0 to 180 so p($\phi_Y$(x,z))=1 for such cases. Conversely, for bright to dark transitions, cost should be high which is achieved by assigning the orientation penalty p($\phi_Y$(x,z)) a value less than 1. Values of p($\phi_Y$(x,z))<1 are computed by linear interpolation.

The term $e_Y$(x,z) in Equation [4] is a thresholding function which suppresses all the nodes/pixels where the first and second image derivatives are below a threshold. $e_Y$(x,z) is defined as:

$$e_Y(x, z) = \begin{cases} p_Y^{min}, & \text{if } \mathcal{M}_{1Y}^{2D}(x, z) < \theta_{1Y}(x, z) \\ & \text{and } \mathcal{M}_{2Y}^{2D}(x, z) < \theta_{2Y}(x, z) \\ 1, & \text{otherwise} \end{cases} \quad [7]$$

where $p_Y^{min} = \min(p(\phi_Y(x,z)))$ ($\geq 0$ from Equation [6]), while $\theta_{1Y}(x,z)$ and $\theta_{2Y}(x,z)$ are adaptive thresholds determined from the gradient information and the values are computed separately for each 2D cross-sectional image 100. $\theta_{1Y}(x,z)$ for a 2D cross-sectional image 100 may be defined such that 95% of the pixels have the absolute value of the first image derivative, $\mathcal{M}_{1Y}^{2D}$, to be less than $\theta_{1Y}(x,z)$. Similarly, $\theta_{2Y}(x,z)$ may be defined using the second image derivative, $\mathcal{M}_{2Y}^{2D}$. The image derivatives may be computed by first blurring the image with Gaussian kernel of size 3×3 followed by convolution with the Scharr operator.

The edge-based parameter $c_Y^{edge}$ uses the gradient information to find points with higher gradients. The cost function of existing methods finds points just above the surface with lower cost. As a result, the skin surface has minor peaks. The thresholding function $e_Y(x,z)$ in Equation [7] assigns a higher cost to these points since gradients there are smaller. Consequently, these minor peaks are removed.

The term $b_Y(x,z)$ in Equation [5] is a measure of the number of bright pixels above each pixel. This term is used to differentiate between a dark to bright transition at the skin surface from those at other locations below the skin surface, thereby helping to overcome false segmentation at the lower layers below the skin surface which could result in inaccurate definition of the skin surface.

The value of $b_Y(x,z)$ at the skin surface is lower than its value below the skin surface because the portion above the skin surface is all dark. The values of $b_Y(x,z)$ is also decreasing from the skin surface to the lower layers of the skin structure. In one example computation of $b_Y(x,z)$, a bright pixel is defined as any pixel with an intensity greater than a threshold, which may be empirically defined as 200.

The term $r_Y(x,z)$ refers to the 2D version of the non-edge-based parameter of the cost function, and is equal to the sum of the inside and outside variances computed for a column of a 2D cross-sectional image 100. The term $r_Y(x,z)$ is defined for a pixel $(x',Y,z')$ as:

$$r_Y(x', z') = \sum_{z \leq z'} (I(x', Y, z) - a_1^2) + \sum_{z > z'} (I(x', Y, z) - a_2^2) \quad [8]$$

where $a_1$ and $a_2$ are constants which can be approximated with $\hat{a}_1(x',Y,z')$ and $\hat{a}_2(x',Y,z')$.

$\hat{a}_1(x',Y,z')$ and $\hat{a}_2(x',Y,z')$ are defined for each pixel/node in the 2D cross-sectional image 100 (at y=Y) as follows:

$$\hat{a}_1(x',Y,z') = \text{mean}(I(x,Y,z_1)) \quad [9]$$

$$\hat{a}_2(x',Y,z') = \text{mean}(I(x,Y,z_2)) \quad [10]$$

where $\mathbb{z}_1 \equiv \{z | z \leq \max(0, z' - |x - x' \Delta_x|)\}$ and $\mathbb{z}_2 \equiv \{z | z' + |x - x' \Delta_x| < z < N_z\}$. Both $b_Y(x,z)$ and $r_Y(x,z)$ are normalized such that their values reside in the same range as that of $c_Y^{edge}(x,z)$.

The cost computation stage 220 thus computes the cost for each pixel of the 2D cross-sectional images 100 and this corresponds to the cost of the voxel at that location. The 3D representation 250 of the skin structure is generated based on the cost assigned to each voxel. The cost of the surface of the skin structure is computed as the sum of the costs of all the voxels lying on it. The step 240 of the method 200 finds the skin surface with the minimum cost by determining the closed set C with the minimum cost, i.e. the minimum-cost closed set, from the 3D graph 230 based on the computed costs.

The cost of the closed set C is the sum of the costs of the nodes 260 contained in the closed set C. This equivalence is achieved by defining the weight of a node V (x, y, z) in the 3D graph 230 or G=(V, E) as:

$$w(x, y, z) = \begin{cases} c(x, y, z), & \text{if } x = 0 \\ c(x, y, z) - c(x, y, z - 1), & \text{otherwise} \end{cases} \quad [11]$$

Once weights are defined at the nodes 260 of the 3D graph 230, the 3D graph 230 becomes a node-weighted directed graph (digraph). As described above in the step 240, the minimum-cost closed set in this digraph can be found using the standard max-flow min-cut algorithm and this set corresponds to the 3D representation 250 of the skin structure or the desired skin structure of the subject.

For evaluation of the effectiveness of the 3D representations 250 generated by the method 200, datasets are constructed for two types of 2D cross-sectional images or slices 100, namely those with hair and those without hair. The first dataset (skin dataset 1 or SD1) consists of 5 OCT volumes 110 without hair. The OCT volumes 110 in SD1 are captured from the palms and soles of subjects or patients at a medical facility or hospital. The second dataset (skin dataset 2 or SD2) consists of 252 2D cross-sectional images 100 extracted from 26 OCT volumes 110 with hair. The OCT volumes 110 in SD2 are captured from the anterior and posterior forearms and the face of the subjects/patients. The 252 2D cross-sectional images 100 are selected through visual inspection of the 26 OCT volumes 110. Only 2D cross-sectional images 100 where hair is visibly prominent are selected. In addition, if there are consecutive or adjacent 2D cross-sectional images 100 which appear similar to each other, only one of these 2D cross-sectional images 100 are selected to avoid compromising the dataset SD2 due to similar-looking images. Each 2D cross-sectional image 100 may be of the size 360×200 pixels. Ground truth, i.e. information from direct observation, for the surface of the skin structure is manually marked for all the 2D cross-sectional images 100 in the datasets SD1 and SD2.

In the generated 3D representation 250 of the skin structure, the intersection of the skin surface with each 2D cross-sectional image 100 has a curvilinear profile. An evaluation of the accuracy of the 3D representation 250 is performed for each 2D cross-sectional image 100. The evaluation includes experiments performed on both the datasets SD1 and SD2. The curvilinear profile for each 2D cross-sectional image 100 is compared to the ground truth. The evaluation metric for a 2D cross-sectional image 100 is the unsigned mean vertical error which is given as:

$$E_u = \frac{1}{N_x} \left( \sum_{x=1}^{N_x} |z_x^{pred} - z_x^{GT}| \right) \quad [12]$$

where $z_x^{pred}$ is the z coordinate for the $x^{th}$ column derived from the curvilinear profile, and $z_x^{GT}$ is the actual z coordinate for the $x^{th}$ column derived from the ground truth or direct observation.

The evaluation results for the method 200 are compared with those for existing methods and are shown in Table 1 below. The values in Table 1 refer to the unsigned mean vertical error. The values in braces are the standard deviations and the best results are underlined. The constants determining smoothness of the skin surface are $\Delta_x=2$ and $\Delta_y=3$ for all the experiments.

TABLE 1

| | SD1 (5 OCT Volumes) | | | | | | SD2 (252 Images) |
|---|---|---|---|---|---|---|---|
| | 1st OCT Volume | 2nd OCT Volume | 3rd OCT Volume | 4th OCT Volume | 5th OCT Volume | Mean | |
| First existing method | 2.12 (0.35) | 1.38 (0.28) | 2.04 (0.32) | 1.68 (0.54) | 1.99 (0.36) | 1.84 | 3.97 (6.45) |
| Second existing method | 1.82 (0.90) | <u>1.21</u> (0.27) | 2.15 (1.95) | <u>1.56</u> (0.94) | 1.49 (0.29) | 1.65 | 3.29 (5.72) |
| Method 200 | <u>1.75</u> (0.32) | 1.53 (0.32) | <u>1.67</u> (0.37) | 1.80 (0.58) | <u>1.41</u> (0.27) | <u>1.63</u> | <u>1.97</u> (0.69) |

The first existing method refers to a 2D graph-based method for skin surface segmentation whereby vertical intensity gradients are used in the cost function. The second existing method refers to a 2D graph-based method whereby vertical intensity gradients and gradient magnitude are used in the cost function.

Figure 6:
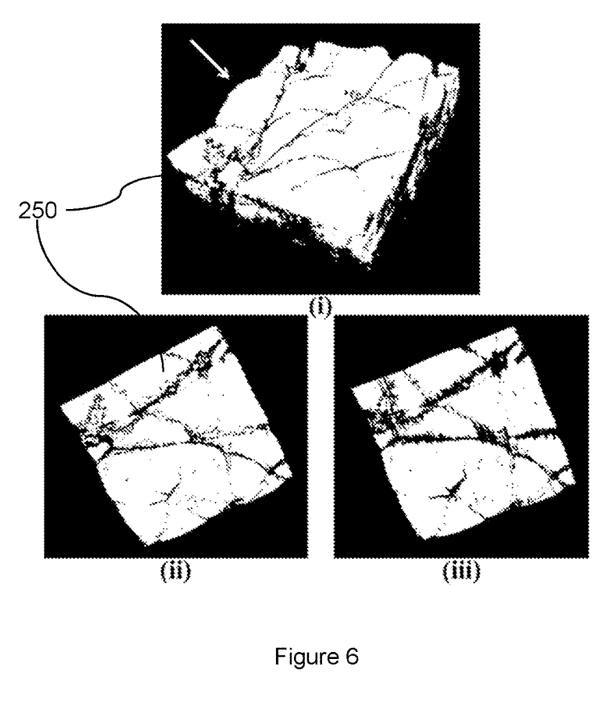
FIG. 6 illustrates various images for comparison of smoothness of 3D representations of the skin structure.

From Table 1, it can be seen that for the dataset SD1, the performance of the 3D representation 250 from the method 200 is almost same as that of the existing methods. This is because introduction of three dimensions only adds an additional connection (in the OCT volume 110) across the 2D cross-sectional images 100, which gives information from neighbouring/adjacent 2D cross-sectional images 100. This information may not be necessary if there is no or minimal presence of hair on the skin surface of the subjects, as is the case for the dataset SD1. The existing methods are able to provide accurate segmentation of the skin structure when there is no hair but this information adds smoothness to the results as illustrated in FIG. 6. Thus, accuracy may not be higher for such cases without hair on the skin surface.

Referring to FIG. 6, image (i) illustrates the 3D representation 250 of the skin structure and surface derived from an OCT volume 110 according to the method 200. Image (ii) illustrates the 3D representation 250 when viewed in the direction of the arrow shown in image (i). Image (iii) illustrates a segmentation of the same OCT volume 110 using an existing 2D method. As seen from FIG. 6, the skin surface of the 3D representation 250 from the method 200 is smoother than that from the existing 2D method, evidently due to the presence of artifacts on the skin surface in image (iii).

For the dataset SD2 wherein there is presence of hair, the effectiveness or advantage of the 3D representation 250 from the method 200 is more apparent and evident by the values shown in Table 1. Due to connections across the 2D cross-sectional images 100, the 3D representation 250 improves smoothness of the skin surface. Even in the presence of hair, the skin surface smoothness is maintained because the hair is not present in all of the 2D cross-sectional images 100. In other words, for some of the 2D cross-sectional images 100, the hair does not touch the skin surface. When the 2D cross-sectional images 100 are considered collectively against one another, the 3D representation 250 becomes less affected by the presence of hair. The effectiveness of the 3D representation 250 is evident by the evaluation results shown in Table 1 as well as the illustrations in FIG. 7.

Figure 7:
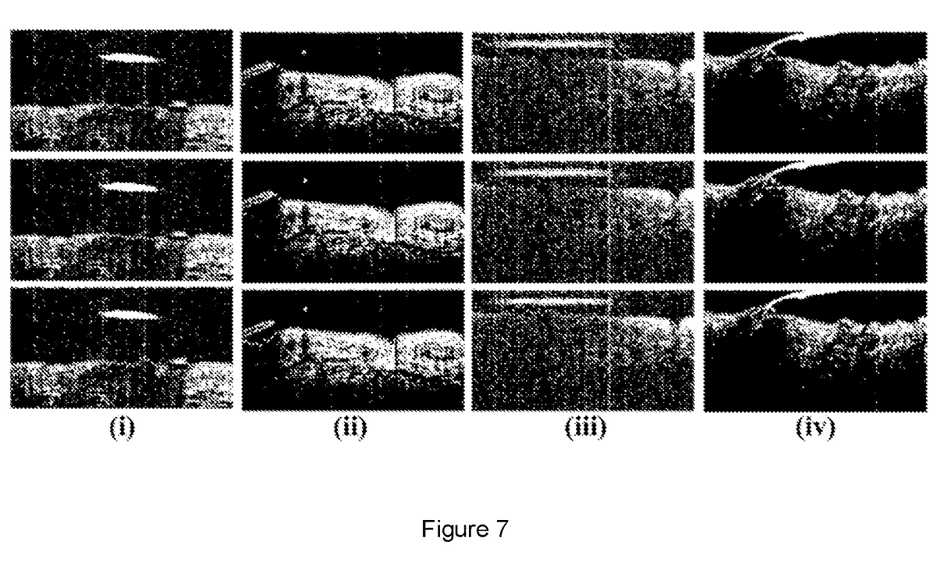
FIG. 7 illustrates evaluation results for various 2D cross-sectional images.

FIG. 7 illustrates evaluation results for four sample 2D cross-sectional images 100. The top row of images is derived from the first existing method. The middle row of images is derived from the second existing method. The bottom row of images is derived from the method 200. The unsigned mean vertical errors for the samples are shown in Table 2 below.

TABLE 2

| | Sample (i) | Sample (ii) | Sample (iii) | Sample (iv) |
|---|---|---|---|---|
| First existing method | 2.03 | 4.81 | 15.96 | 3.38 |
| Second existing method | 1.00 | 4.09 | 10.96 | 3.24 |
| Method 200 | 0.97 | 2.28 | 2.63 | 2.38 |

As evident from FIG. 7 and Table 2, the method 200 outperformed the existing methods as the unsigned mean vertical errors are the lowest. Consequently, the reduction in error is more than 39% as compared to the existing methods (Table 1).

The 3D representation 250 of the skin structure generated by the method 200 thus enables for more accurate analysis of the skin structure and surface. The 3D representation 250 is formed from multiple 2D cross-sectional images 110 such that information from neighbouring/adjacent images 100 is considered. Since a single instance of hair is usually present in only a few consecutive images 100, collective consideration of all the images 100 attenuate the effects of hair presence in some of the images 100, resulting in a more accurate representation of the skin structure and surface.

The method 200 and the generated 3D representation 250 of the skin structure can be applied for assessment of skin conditions. For example, in the cosmetics, pharmaceuticals, and/or cosmeceuticals areas, the method 200 can be used as a potential tool for assessing the efficacy of products for skin smoothing. The method 200 may be performed by the system, e.g. including a skin OCT machine, to provide analytical functionality to acquired OCT volumes 110.

In some embodiments, there is provided an automatic skin surface topographic analysis system for dermatological and cosmeceutical practice (ASHIGA). The ASHIGA system automatically analyzes high-definition OCT (HD-OCT) images, i.e. the 2D cross-sectional images 100 of the skin structures of subjects, and evaluates the skin surface topography using a set of roughness parameters. Computation of the roughness parameters provides dermatologists/clinicians an immediate and objective assessment of a subject's skin roughness.

Figure 8:
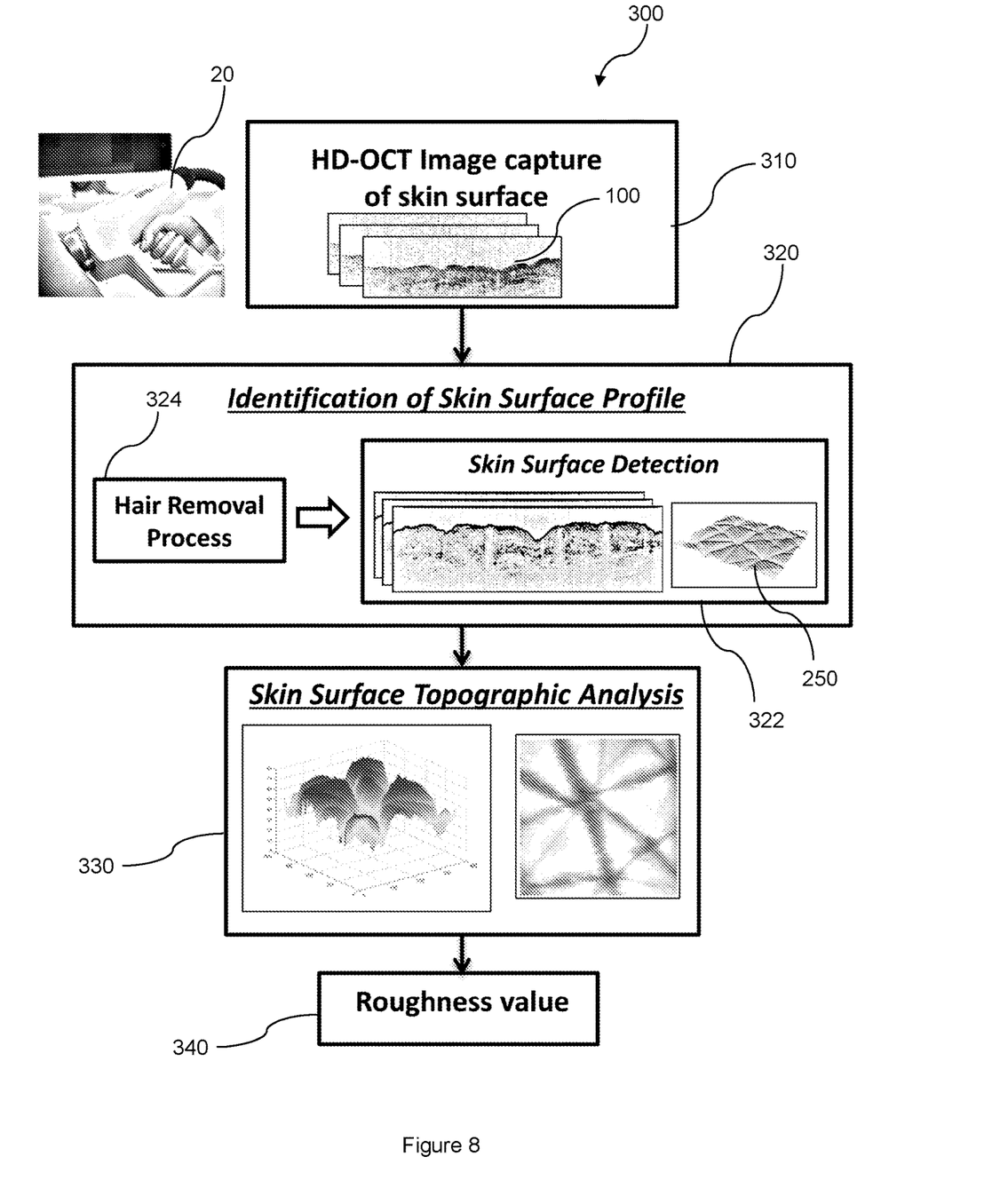
FIG. 8 illustrates a flowchart of a method for assessing skin roughness of a subject.

With reference to FIG. 8, there is a method 300 performed by the ASHIGA system for assessing skin roughness of a subject based on the 3D representation 250. The method 300 includes a step 310 of capturing, by an OCT apparatus 20, the 2D cross-sectional images 100 of the skin structure and surface of the subject. The method 300 further includes a step 320 of identifying the skin surface profile. The step 320 includes performing the method 200 to generate a 3D representation 250 of the skin structure and surface. The step 320 further includes a sub-step 322 of detecting the skin surface profile from the 3D representation 250. Optionally, the step 320 may include a sub-step 324 of removing hair from the skin surface of the subject beforehand. However, this sub-step 324 is unnecessary because, as described above, the presence of hair does not adversely affect or compromise the results of further analysis on the skin surface. Moreover, presence of hair on the skin surface can be digitally removed by segmenting the skin surface profile of the 3D representation 250, enabling the ASHIGA system to provide for more accurate analyses.

The method 300 further includes a step 330 of performing skin surface topographic analysis on the skin surface detected from the 3D representation 250. In a subsequent step 340, values for a set of roughness parameters are computed. The method 300 thus automatically processes the 2D cross-sectional images 100, evaluate the roughness of the skin surface detected from the 3D representation 250, and compute the values for the set of roughness parameters for evaluation of the skin surface roughness.

Figure 9A:
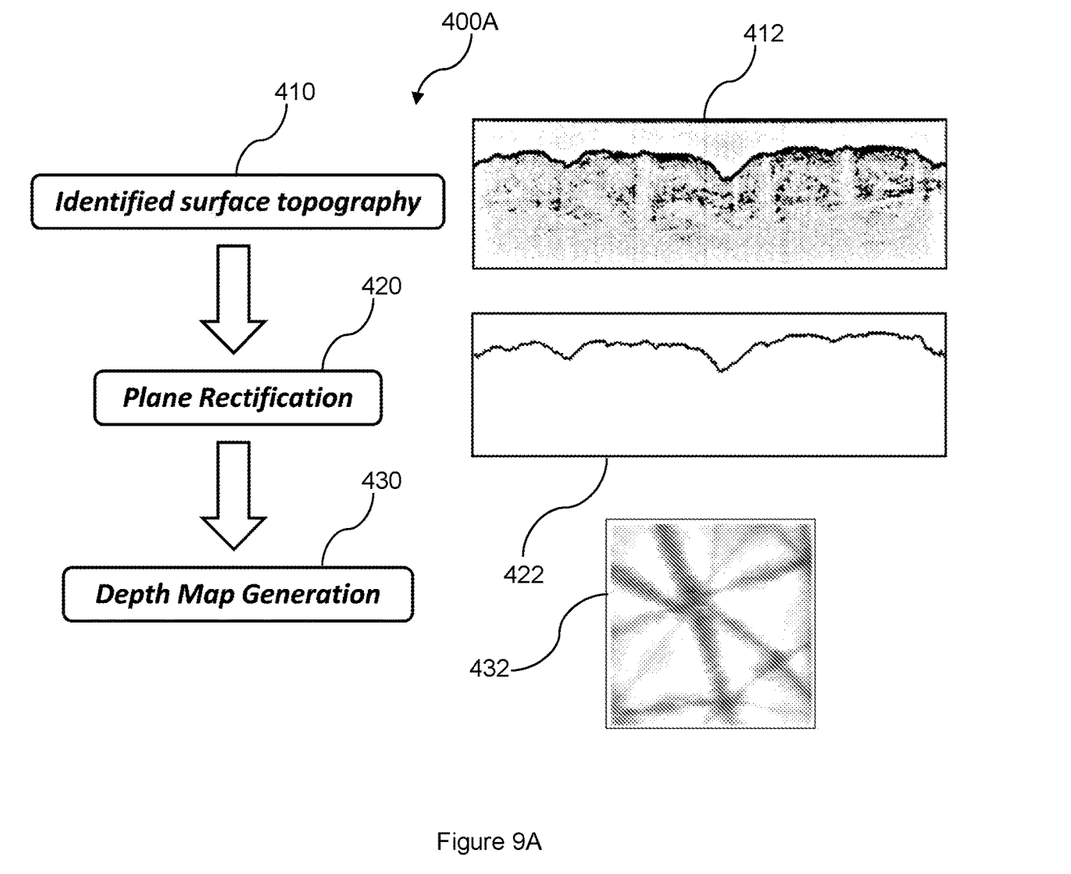
FIG. 9A illustrates an example of a skin surface topographic analysis for assessing skin roughness.

In one embodiment with reference to FIG. 9A, there is a skin surface topographic analysis 400A performed in in the step 330 of the method 300. In another embodiment with reference to FIG. 9B, there is a skin surface topographic analysis 400B performed in in the step 330 of the method 300. Each of FIGS. 9A and 9B illustrates the process flow of the skin surface topographic analyses 400A and 400B, respectively, to analyze the skin surface topography for computing the roughness parameters in the step 340.

The skin surface topographic analysis 400A/400B includes a step 410 of identifying or detecting the skin surface topography 412 from the 3D representation 250 of the skin structure. Notably, the step 410 is equivalent of the sub-step 322 described above. As the various areas of the skin surface topography 412 are not on the same plane, the skin surface topographic analysis 400A/400B includes a plane rectification process 420 to correct the planes for the various areas of the skin surface topography 412 to a common plane, thereby generating a plane-rectified skin surface topography 422. The skin surface topographic analysis 400A/400B further includes a depth map generation process 430 for generating a 2D depth map 432 based on the plane-rectified skin surface topography 422.

The 2D cross-sectional images 100 are captured by an imaging probe of the OCT apparatus 20 that produces en face images of size 640×512. However, there is a noticeable signal falloff at the edges of the imaging field of view. It is empirically observed that the signal within a circular region is of better quality compared to the signal outside the circular region. Hence, the size of the 2D depth map is defined as 360×360, which is the maximum inscribed square to avoid noticeable signal falloff.

Figure 9B:
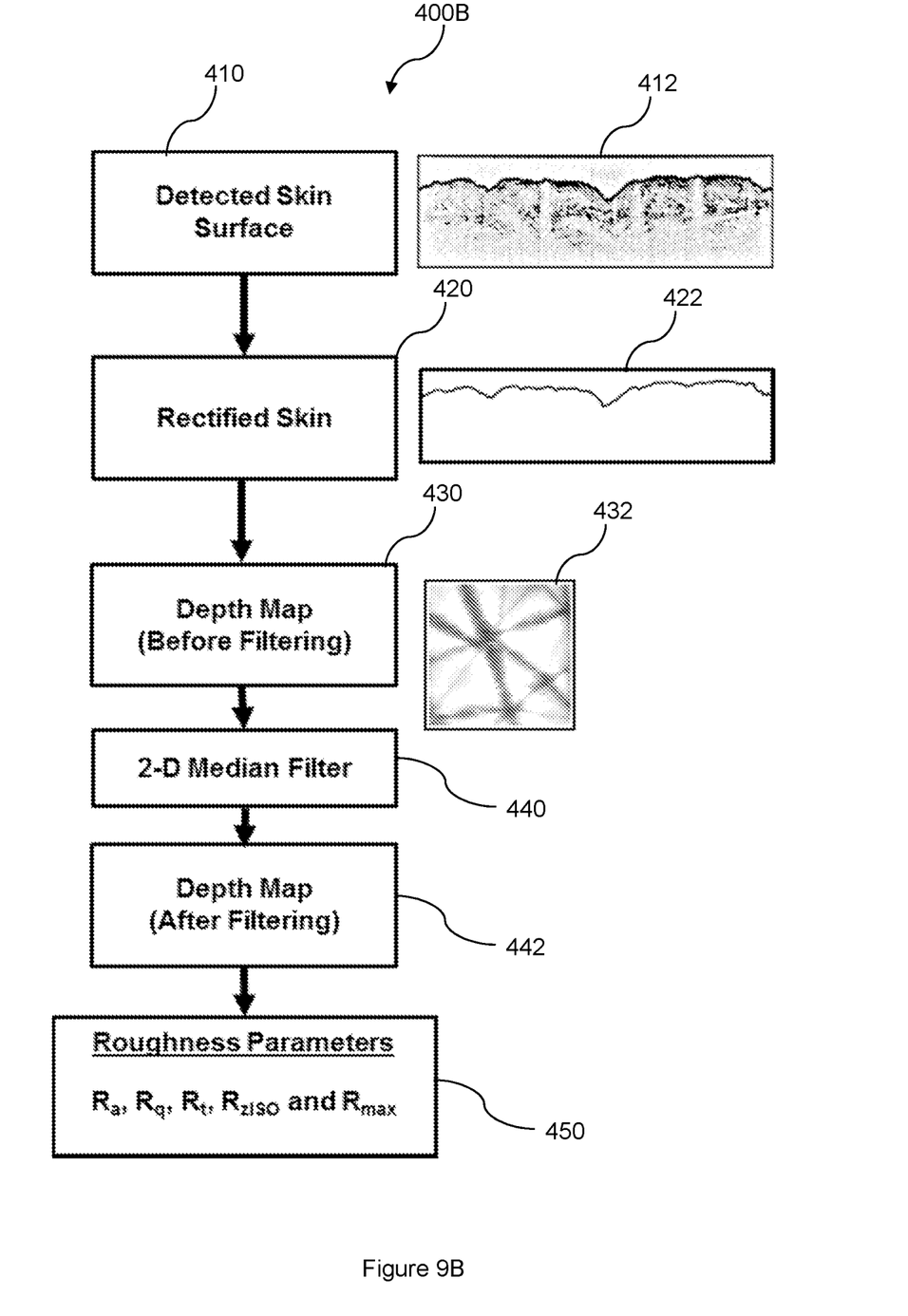
FIG. 9B illustrates another example of a skin surface topographic analysis for assessing skin roughness.

In the skin surface topographic analysis 400B as shown in FIG. 9B, the 2D depth map 432 may be subject to an additional 2D median filter process 440. A filtered 2D depth map 442 is consequently generated. The 2D median filter process 440 may be performed on the unfiltered 2D depth map 432 to remove noise therefrom.

In a step 450, the roughness parameters are computed based on the 2D depth map 432. It will be appreciated that, in another embodiment, the roughness parameters may be computed based on the filtered 2D depth map 442. It will also be appreciated that the step 450 is equivalent to the step 340 of the method 300.

Skin surface topography can be described with the roughness parameters defined by the International Organization for Standardization (ISO) in ISO 4287-1977. The roughness parameters can be catergorized into two types—amplitude and frequency parameters. In the skin surface topography analysis 400A/400B to assess the roughness of the skin surface, five amplitude parameters $R_a$, $R_q$, $R_t$, $R_{zISO}$, and $R_{max}$ are used as the roughness parameters.

Figure 10:
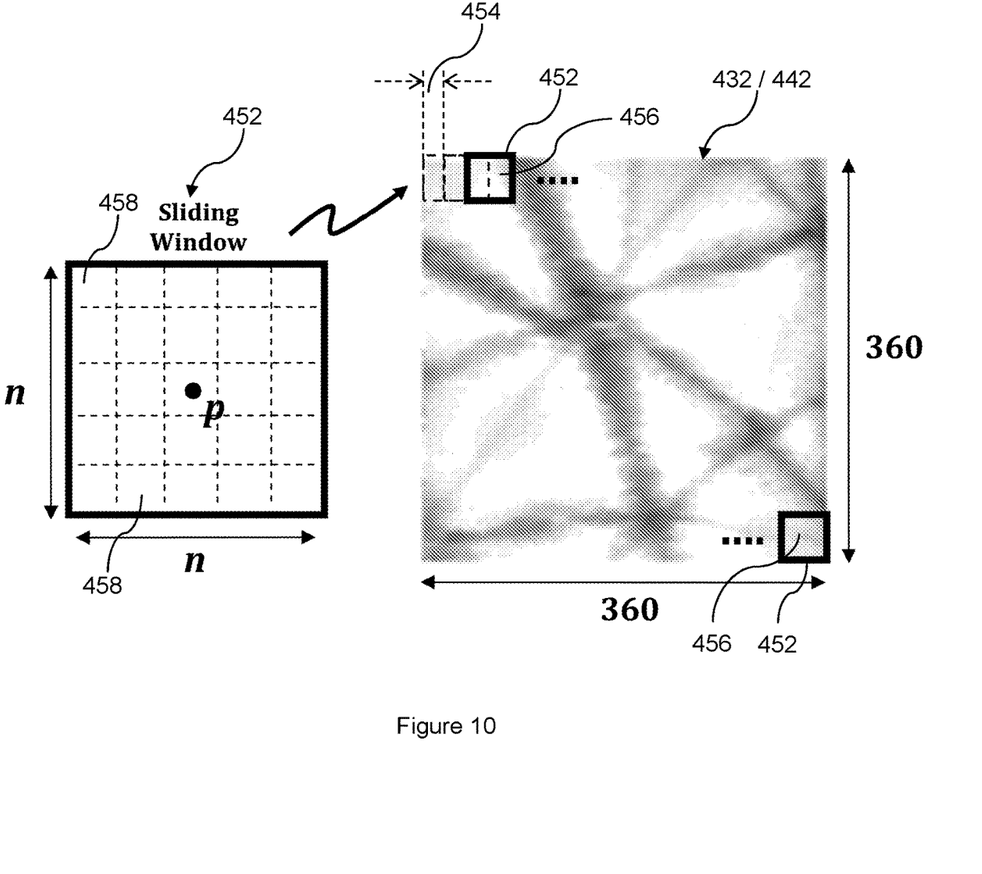
FIG. 10 illustrates a sliding window approach in the skin surface topographic analysis.

As shown in FIG. 10, a sliding window approach on the 2D depth map 432 is used to compute/calculate the roughness parameters. The sliding window 452 is set to a size of n×n, where the reference point, p is always at the centre of the sliding window 452. The sliding window 452 is moved across a plurality of discrete steps 454 over the 2D depth map 432 until the entire area of the 2D depth map 432 has been scanned by the sliding window 452. It will be appreciated that the discrete steps 454 may be defined such that there is an overlap between every pair of consecutive sliding windows 452.

For each discrete step 454 wherein the sliding window 452 is placed over a window area 456 of the 2D depth map 432, the five roughness parameters are computed and the computed results define the local (said window area 456 of the 2D depth map 432) values of of $R_a$, $R_q$, $R_t$, $R_{zISO}$, and $R_{max}$ at the centre p.

The first roughness parameter $R_a$ refers to the average deviation of depth profile over each window area 456, and is defined as follows:

$$R_a = \frac{1}{N}\sum_{n=1}^{N}|r_n| \quad [13]$$

where N is the number of pixels in the window area 456 and $r_n$ is the depth value at each pixel.

The second roughness parameter $R_q$ refers to the root-mean-square average roughness in the window area 456, and is defined as follows:

$$R_q = \sqrt{\frac{1}{N}\sum_{n=1}^{N}r_n^2} \quad [14]$$

The third roughness parameter $R_t$ refers to the sum of the maximum depth value and minimum depth value in the window area 456, and is defined as follows:

$$R_t = |\max\,[r_n]| + |\min\,[r_n]| \quad [15]$$

The fourth roughness parameter $R_{zISO}$ is a parameter that averages the sum of five highest peaks height and five deepest valleys depth over the evaluation length. $R_{zISO}$ is defined as follows:

$$R_{zISO} = \frac{1}{5}\left(\sum_{n=1}^{5}|\max[r_n]| + \sum_{n=1}^{5}|\min[r_n]|\right) \quad [16]$$

The fifth roughness parameter $R_{max}$ is a parameter which serves a purpose similar to $R_t$. $R_{max}$ determines the extreme peak-to-valley length from five sampling lengths. Within the window area 456, the window area 456 is sub-divided into smaller regions or patches. The sliding window 452 may be similarly sub-divided into the same number of smaller regions or patches 458 as shown in FIG. 10. Each region 458 may have a size of n/5×n/5, and $R_t$ is computed for each patch 458. The highest value of $R_t$ among all the regions 458 is defined as the $R_{max}$ for the window area 456.

Experiments are performed on various sets of test images for assessing skin roughness. The calculated roughness parameters for different window sizes n×n are shown in Tables 3A to 3C below. The experimental results show that the roughness parameters are insensitive to window sizes of n=20, n=30, and n=40.

TABLE 3A

| Test Images | Mean Subjective Ranking | n × n = 20 × 20 | | | | |
|---|---|---|---|---|---|---|
| | | $R_a$ | $R_q$ | $R_t$ | $R_{zISO}$ | $R_{max}$ |
| Set 1 IMG01 | 3 | 2.72 | 3.29 | 14.30 | 13.52 | 4.61 |
| IMG02 | 2 | 1.11 | 1.37 | 6.55 | 6.05 | 2.83 |
| IMG03 | 1 | 0.80 | 1.02 | 5.17 | 4.67 | 2.40 |
| Set 2 IMG04 | 1.3 | 0.95 | 1.18 | 5.80 | 5.32 | 2.59 |
| IMG05 | 2.4 | 2.82 | 3.40 | 14.90 | 14.05 | 5.12 |
| IMG06 | 2.3 | 1.97 | 2.38 | 10.57 | 9.92 | 3.68 |
| Set 3 IMG07 | 3 | 2.81 | 3.42 | 15.36 | 14.45 | 5.31 |
| IMG08 | 1.75 | 2.40 | 2.91 | 13.21 | 12.34 | 4.71 |
| IMG09 | 1.25 | 2.06 | 2.52 | 11.31 | 10.60 | 3.66 |

TABLE 3B

| Test Images | Mean Subjective Ranking | n × n = 30 × 30 | | | | |
|---|---|---|---|---|---|---|
| | | $R_a$ | $R_q$ | $R_t$ | $R_{zISO}$ | $R_{max}$ |
| Set 1 IMG01 | 3 | 3.59 | 4.32 | 19.24 | 18.49 | 6.69 |
| IMG02 | 2 | 1.31 | 1.63 | 8.42 | 7.91 | 3.78 |
| IMG03 | 1 | 0.93 | 1.18 | 6.63 | 6.10 | 3.13 |
| Set 2 IMG04 | 1.3 | 1.13 | 1.41 | 7.46 | 6.98 | 3.39 |
| IMG05 | 2.4 | 3.71 | 4.46 | 19.85 | 19.05 | 7.32 |
| IMG06 | 2.3 | 2.56 | 3.09 | 14.12 | 13.49 | 5.19 |
| Set 3 IMG07 | 3 | 3.68 | 4.47 | 20.76 | 19.88 | 7.71 |
| IMG08 | 1.75 | 3.14 | 3.79 | 17.58 | 16.75 | 6.69 |
| IMG09 | 1.25 | 2.67 | 3.25 | 14.98 | 14.31 | 5.38 |

TABLE 3C

| Test Images | Mean Subjective Ranking | n × n = 40 × 40 | | | | |
|---|---|---|---|---|---|---|
| | | $R_a$ | $R_q$ | $R_t$ | $R_{zISO}$ | $R_{max}$ |
| Set 1 IMG01 | 3 | 4.33 | 5.21 | 23.41 | 22.68 | 8.63 |
| IMG02 | 2 | 1.49 | 1.86 | 10.12 | 9.59 | 4.60 |
| IMG03 | 1 | 1.05 | 1.33 | 7.92 | 7.37 | 3.77 |
| Set 2 IMG04 | 1.3 | 1.30 | 1.62 | 9.01 | 8.51 | 4.08 |
| IMG05 | 2.4 | 4.47 | 5.37 | 24.04 | 23.25 | 9.40 |
| IMG06 | 2.3 | 3.06 | 3.70 | 17.27 | 16.65 | 6.61 |
| Set 3 IMG07 | 3 | 4.43 | 5.38 | 25.42 | 14.45 | 5.31 |
| IMG08 | 1.75 | 3.78 | 4.56 | 21.30 | 12.34 | 4.71 |
| IMG09 | 1.25 | 3.16 | 3.84 | 18.04 | 10.60 | 3.66 |

Existing skin surface topography evaluation techniques such as replica-based methods have limitations, which may result in errors and inaccurate measurements. The ASHIGA system described in the method 300 provides an objective skin surface topography assessment tool using the 2D cross-sectional images 100, e.g. HD-OCT images acquired by the OCT apparatus 20, which is a type of non-invasive skin image modality used clinically. The ASHIGA system can also be embedded in skin OCT manufacturers to provide analytical functionality to acquired raw OCT or HD-OCT images.

The ASHIGA system may be used in skin and dermatology clinics for assessment of skin conditions, e.g. roughness. The ASHIGA system may also be a potential tool for the cosmetics, pharmaceuticals, and/or cosmeceuticals fields to assess efficacy of products for skin smoothing.

Some of the advantages of the ASHIGA system over the existing methods include, but are not limited to, the following:

Automated system that enables objective and fast assessment of skin characteristics, e.g. roughness.

Enables on-site assessment of skin roughness for immediate feedback to dermatologists/clinicians and subjects/patients.

Independent of lighting conditions and other external/environmental factors which the existing methods are more sensitive to, such as body movements and distortions of replicas.

Independent quantification of skin roughness that is consistent with findings from dermatologists/clinicians and observers.

Operates on single set of scan data; does not require additional scans or procedures unlike the skin replica assessment technique.

In the foregoing detailed description, embodiments of the present disclosure in relation to an automated method and system for generating a 3D representation of a skin structure of a subject are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

What is claimed is:

1. An automated method for generating a three-dimensional (3D) representation of a skin structure of a subject, the method comprising:
   acquiring a plurality of two-dimensional (2D) cross-sectional images of the skin structure, each 2D cross-sectional image comprising a skin surface profile;
   computing a cost for each 2D cross-sectional image based on a cost function, the cost function comprising an edge-based parameter associated with gradient information of the skin surface profile and a non-edge-based parameter associated with homogeneity information of the 2D cross-sectional image above and below the skin surface profile;
   constructing a 3D graph from the 2D cross-sectional images; and
   determining a minimum-cost closed set from the 3D graph based on the computed costs for the 2D cross-sectional images, wherein the 3D representation of the skin structure comprising the skin surface profile is generated from the minimum-cost closed set.

2. The method according to claim 1, wherein computing the costs for the 2D cross-sectional images comprises computing a cost for each pixel of each 2D cross-sectional image.

3. The method according to claim 1, further comprising performing skin topographic analysis on the 3D representation to assess skin roughness of the subject.

4. The method according to claim 3, wherein the skin topographic analysis comprises performing a plane rectification process.

5. The method according to claim 4, wherein the skin topographic analysis further comprises generating a 2D depth map.

6. The method according to claim 5, wherein the skin topographic analysis further comprises computing a set of roughness parameters.

7. The method according to claim 6, wherein the roughness parameters are calculated based on a sliding window approach on the 2D depth map.

8. The method according to claim 6, wherein the set of roughness parameters comprises amplitude and frequency parameters.

9. A system for generating a three-dimensional (3D) representation of a skin structure of a subject, the system comprising a processor configured for performing operations comprising:
acquiring a plurality of two-dimensional (2D) cross-sectional images of the skin structure, each 2D cross-sectional images comprising a skin surface profile;
computing a cost for each 2D cross-sectional image based on a cost function, the cost function comprising an edge-based parameter associated with gradient information of the skin surface profile and a non-edge-based parameter associated with homogeneity information of the 2D cross-sectional image above and below the skin surface profile;
constructing a 3D graph from the 2D cross-sectional images; and
determining a minimum-cost closed set from the 3D graph based on the computed costs for the 2D cross-sectional images,
wherein the 3D representation of the skin structure comprising the skin surface profile is generated from the minimum-cost closed set.

10. The system according to claim 9, wherein computing the costs for the 2D cross-sectional images comprises computing a cost for each pixel of each 2D cross-sectional image.

11. The system according to claim 9, wherein the non-edge-based parameter is associated with a measure of a dark to bright transition at the skin surface profile.

12. The system according to claim 9, the operations further comprising performing a skin topographic analysis on the 3D representation to assess skin roughness of the subject.

13. The method according to claim 1, wherein the edge-based parameter comprises an orientation penalty function based on gradient orientation.

14. The method according to claim 13, wherein the edge-based parameter further comprises a thresholding function that suppresses pixels where a first image derivative is below a first threshold and a second image derivative is below a second threshold.

15. The method according to claim 14, further comprising computing the first and second image derivatives using a Gaussian kernel and a Scharr operator.

16. The method according to claim 1, wherein the non-edge-based parameter is associated with a measure of a dark to bright transition at the skin surface profile.

17. The method according to claim 16, wherein the non-edge-based parameter is associated with a measure of a number of bright pixels above each pixel.

18. The system according to claim 9, wherein the edge-based parameter comprises an orientation penalty function based on gradient orientation.

19. The system according to claim 18, wherein the edge-based parameter further comprises a thresholding function that suppresses pixels where a first image derivative is below a first threshold and a second image derivative is below a second threshold.

20. The system according to claim 11, wherein the non-edge-based parameter is associated with a measure of a number of bright pixels above each pixel.

* * * * *